(12) United States Patent
Mooney

(10) Patent No.: US 8,905,954 B2
(45) Date of Patent: Dec. 9, 2014

(54) SYSTEMS AND METHODS FOR PROVIDING A CHANNEL THROUGH AN ORTHOPEDIC CAST

(76) Inventor: James Mooney, Hummelstown, PA (US)

( * ) Notice: Subject to any disclaimer, the term of this patent is extended or adjusted under 35 U.S.C. 154(b) by 125 days.

(21) Appl. No.: 13/511,491

(22) PCT Filed: Aug. 18, 2011

(86) PCT No.: PCT/US2011/048175
§ 371 (c)(1),
(2), (4) Date: May 23, 2012

(87) PCT Pub. No.: WO2013/025217
PCT Pub. Date: Feb. 21, 2013

(65) Prior Publication Data
US 2013/0046217 A1    Feb. 21, 2013

(51) Int. Cl.
*A61F 5/00*    (2006.01)
*A61F 13/04*    (2006.01)

(52) U.S. Cl.
CPC ........................... *A61F 13/04* (2013.01)
USPC .................. 602/5; 602/14; 604/174; 604/176

(58) Field of Classification Search
CPC ........... A61F 5/00; A61F 5/01; A61F 5/4408; A61F 5/449; A61F 13/04; A61F 13/046; A61M 3/0266; A61M 3/027; A61M 25/002; A61M 25/02; A61M 2025/02; A61M 2025/0206; A61M 2025/028
USPC ............ 602/5, 14, 900; 604/174, 176, 27, 48, 604/93.01; 128/877, 898; 206/205, 207, 206/210
See application file for complete search history.

(56) References Cited

U.S. PATENT DOCUMENTS

| | | | |
|---|---|---|---|
| 3,998,220 A | 12/1976 | Cleer | |
| 4,596,566 A * | 6/1986 | Kay | ............................. 604/343 |
| 4,827,916 A * | 5/1989 | Kosova | ........................... 602/14 |
| 4,898,160 A | 2/1990 | Brownlee | |
| 5,865,772 A | 2/1999 | George | |
| 6,086,008 A | 7/2000 | Gray | |
| 2009/0071851 A1 | 3/2009 | Maki | |

* cited by examiner

*Primary Examiner* — Patricia Bianco
*Assistant Examiner* — Keri J Nelson
(74) *Attorney, Agent, or Firm* — Puget Patent; Michael Gibbons

(57) ABSTRACT

An appliance which removably stores a portion of a catheter and an adapter, where the indwelling portion of catheter is still inside the body tissue of a patient. The appliance has an aperture that permits connection of a vacuum source such as hospital suction. When the appliance containing the catheter is held against the portion of the body including the indwelling site of the catheter, the vacuum source is applied, having a tendency to hold the appliance in place against the body. An orthopedic cast can be fabricated around the appliance, after which time the vacuum can be deactivated and the appliance can be removed, revealing a channel formed in the orthopedic cast. Through the channel, the distal portion of the catheter and the adapter can be accessed, facilitating continued postoperative anesthesia, easy visual inspection for signs of infection or dislodgment of the catheter and permitting easy removal when needed.

16 Claims, 10 Drawing Sheets

DEPICTION OF PRIOR ART

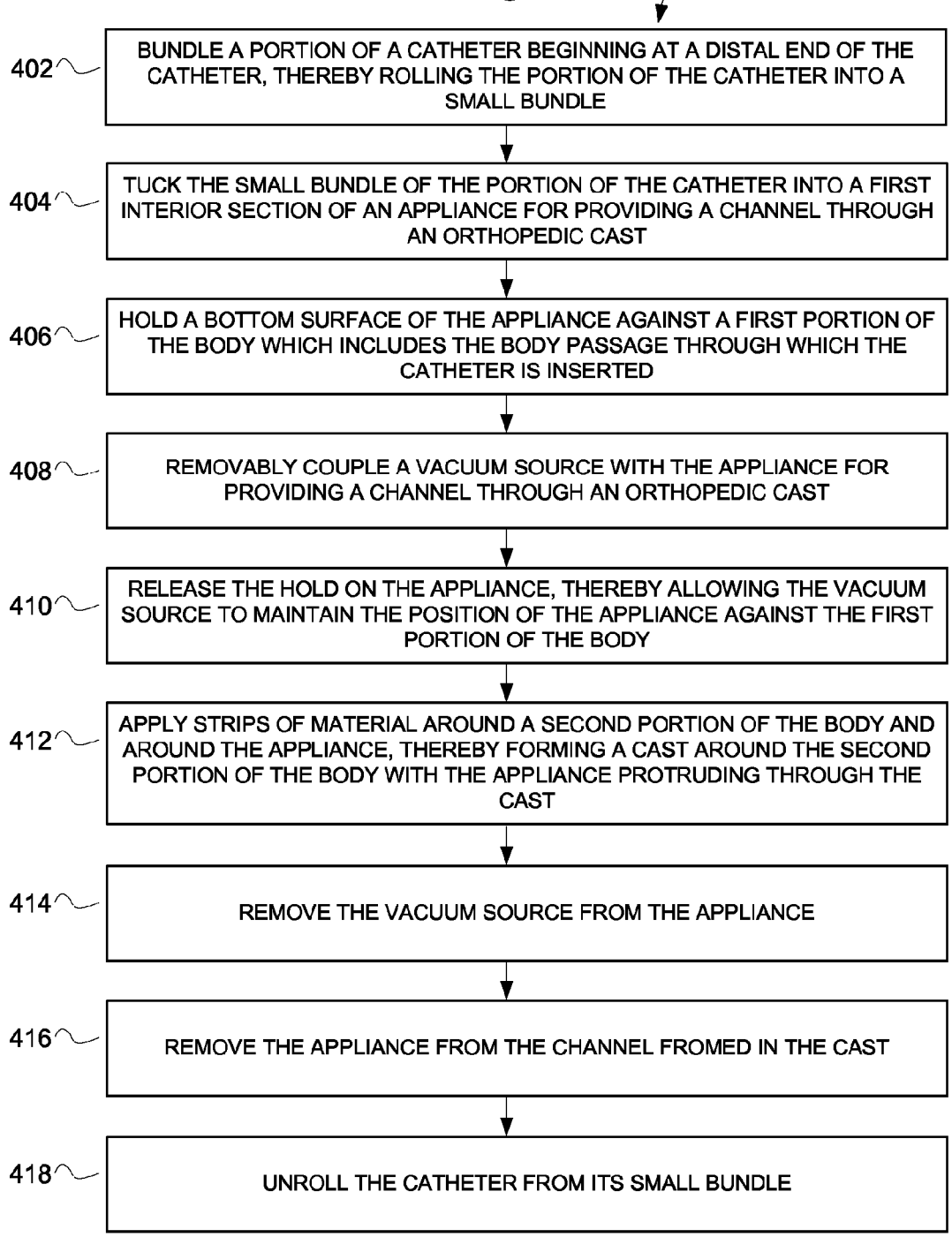

SYSTEMS AND METHODS FOR PROVIDING A CHANNEL THROUGH AN ORTHOPEDIC CAST

PRIORITY CLAIM

This application claims the benefit of PCT application serial number US/2011/048175 filed Aug. 18, 2011. The foregoing application is incorporated by reference in its entirety as if fully set forth herein.

BACKGROUND

An orthopedic cast is used to protect and immobilize a portion of the human body. Often, an orthopedic cast is applied following a procedure to set one or more broken bones. In such cases, the portion of the body with the broken bone is encased in the orthopedic cast, holding the bone fragments in place so that the bone can heal. Other names by which an orthopedic cast is commonly known include a surgical cast, or often simply a cast.

The orthopedic cast is formed by wrapping cotton strips saturated with wet plaster of paris around the portion of the body with the broken bone. When the wet plaster dries, the hardened cast is formed. Other techniques or materials for constructing the cast are available, such as the use of thermoplastic- or fiberglass-infused bandages, but irrespective of the construction the desired end result is a hard shell about a limb or other portion of the human body that immobilizes and protects in order for a broken bone to heal. Casts can be used for conditions other than broken bones as well, including following repair of ligaments or other structures in the body.

Casts come in a variety of shapes. They may cover only a portion of a limb, or they can cover a larger portion of the body. For example, a spica cast is a cast which surrounds the trunk of the body and one or more limbs, and a hip spica cast is a cast surrounding the trunk of the body and one or both legs. Larger casts such as the hip spica are used, for example, where there has been a complex fracture requiring extensive surgery, or following surgery on a child to remedy a congenital dislocation of the hip. Other conditions requiring a larger cast, such as a spica cast, during healing are known.

In instances where an extensive surgery to repair a complex break or a congenital dislocation is required, it is often desirable to continue anesthesia to the patient following the surgery. Following the surgery and once the patient has awakened from the general anesthesia, a continuous infusion of local anesthesia to the area operated on can be delivered for post-operative pain relief. This technique is advantageous because it offers more granular control of pain, while reducing exposure to narcotic pain-killers and their side effects. The local anesthesia is delivered post-operatively utilizing the same nerve catheter used to numb the operative area during the surgery.

An issue can arise when the cast covering the operative area is fabricated, however, as the cast must also cover the site of the passage of the catheter into the body, where the catheter enters the body tissue. Once the cast hardens, the lumen of the catheter runs underneath the cast to the edge where it exits the cast. The site where the catheter enters the body, however, is completely covered underneath the hardened cast.

Covering the portion of the catheter that enters the body with the cast means that the site where the catheter enters the body can not be viewed during the post-operative delivery of anesthesia. Any visual indications of infection at the site are invisible. Additionally, if the anesthesia does not seem to be working well, there is no way to tell whether the catheter has become dislodged. Finally, at the end of hospitalization and before the patient goes home, it is difficult to remove the catheter, being buried under the cast.

What is needed is a manner of leaving a channel in a cast when the cast is fabricated. Such a channel would permit viewing of the site where the catheter enters the body tissue to enable a visual check for infections or dislodgment of the catheter. The channel would also permit easy access to the catheter for removal prior to the patient being sent home.

The cast and channel would be formed around the very nerve catheter inserted pre-operatively for local anesthesia, allowing the catheter to remain in place throughout the surgery, construction of the cast, and subsequent post-operative recovery. Such a channel could also be used for other devices or tubes which would be desirable to run through, rather than underneath, a cast. These other devices or tubes that could run through a channel in the cast might include a pre-existing drain or feeding tube, among other possibilities. But for the greatest structural integrity of the cast, the channel through the cast would need to be as small as possible.

Accordingly, this application discloses systems and methods for providing a channel through an orthopedic cast.

FIELD OF THE INVENTION

This invention relates generally to orthopedic casts, and more specifically, to systems and methods for providing a channel through an orthopedic cast.

SUMMARY

This invention relates generally to orthopedic casts, and more specifically, to systems and methods for providing a channel through an orthopedic cast. In some embodiments, an appliance for providing a channel through an orthopedic cast may have a generally oval shape, with a pair of flattened opposing sides, and a pair of curved opposing ends one of which is a catheter end and one of which is a vacuum end. In some embodiments, an appliance for providing a channel through an orthopedic cast may have a top surface and a bottom surface. In a preferred embodiment, an appliance for providing a channel through an orthopedic cast may have a bottom opening in the bottom surface, leading to a first interior section. In this embodiment, a portion of the catheter is rolled into a bundle, the bundle including an adapter and the distal end of the catheter, with the bundle being placed inside the first interior section. Then, the appliance is held against the patient, the appliance being held over the top of the body passage of the patient where the indwelling portion of the catheter is situated. A vacuum source is coupled to the appliance to keep the appliance in place while a cast is fabricated around a portion of the body of the patient.

In some embodiments, when a cast has been fabricated, the vacuum source is deactivated. Following the deactivation of the vacuum source, the appliance, with the bundle of the portion of the catheter and the adapter contained in the first interior section of the appliance, is removed from the cast, revealing a channel in the formed cast. Following removal of the appliance from the cast by pulling the appliance away from the patient, the bundle of the portion of the catheter and the adapter is removed from the first interior section of the appliance. Anesthesia can then be delivered to the patient by rejoining the connection between the infusion pump and the adapter, and activating the infusion pump.

BRIEF DESCRIPTION OF THE DRAWINGS

Embodiments of the present invention are described in detail below with reference to the following drawings:

FIG. 15 is a flow diagram of a method, in accordance with an embodiment of the invention.

DETAILED DESCRIPTION

This invention relates generally to orthopedic casts, and more specifically, to systems and methods for providing a channel through an orthopedic cast. Specific details of certain embodiments of the invention are set forth in the following description and in FIGS. 1-15 to provide a thorough understanding of such embodiments. The present invention may have additional embodiments, may be practiced without one or more of the details described for any particular described embodiment, or may have any detail described for one particular embodiment practiced with any other detail described for another embodiment.

Figure 1:
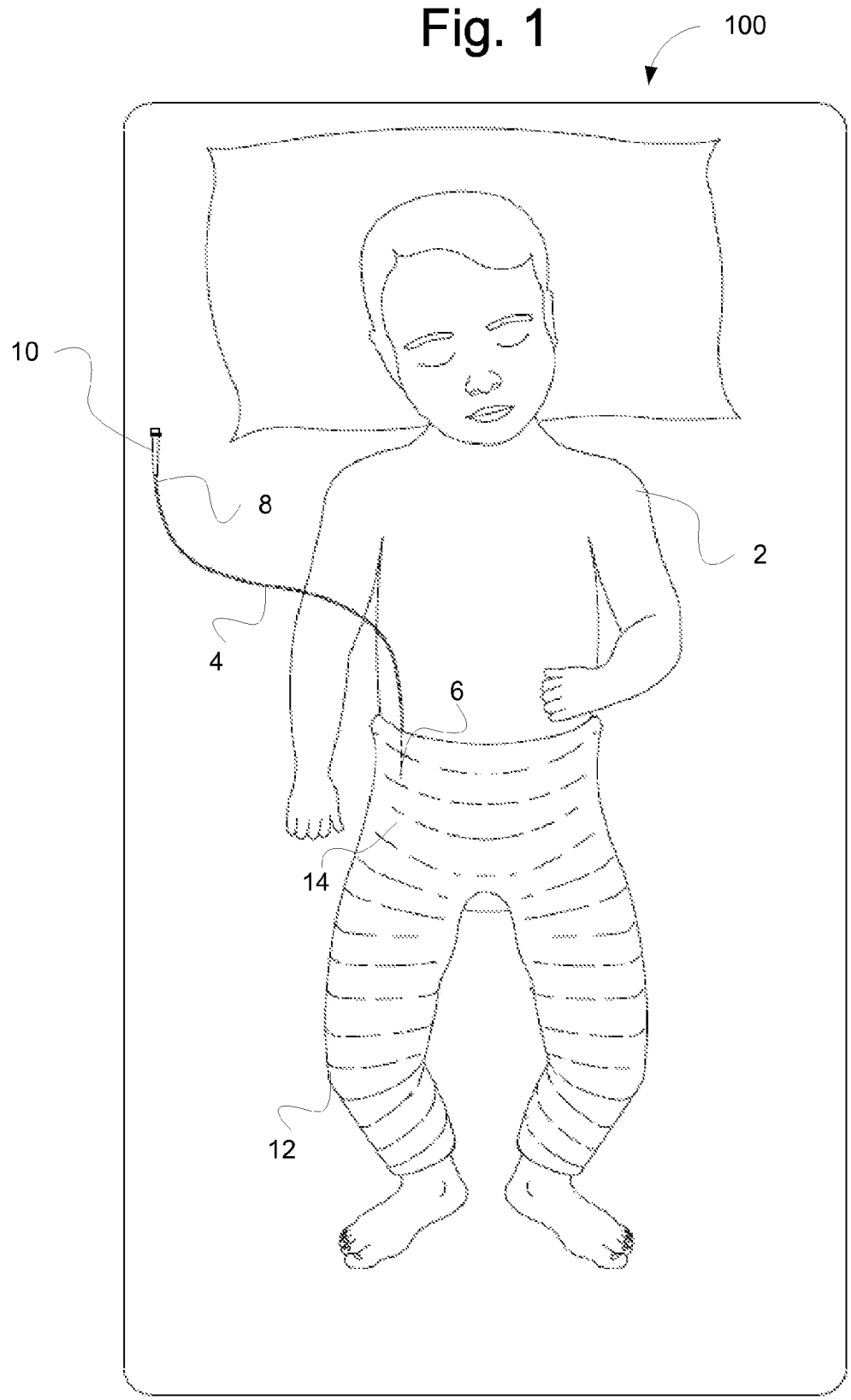
FIG. 1 is a depiction of the prior art, in this case, a perspective view of an exemplary orthopedic cast.
Figure 2:
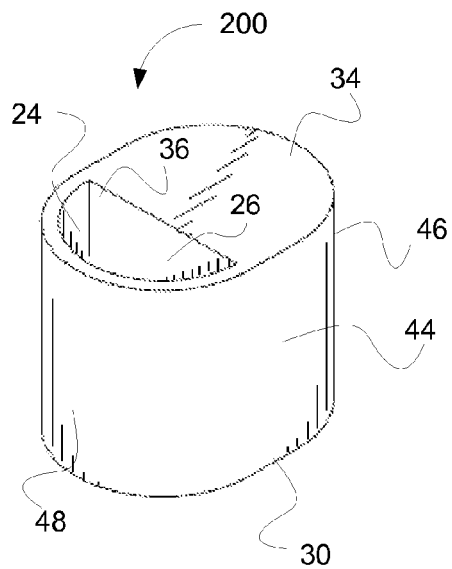
FIG. 2 is a perspective view of an appliance for providing a channel through an orthopedic cast, in accordance with an embodiment of the invention.

FIG. 1 is a depiction of the prior art, in this case, a perspective view of an exemplary orthopedic cast. At 100, a child recovering from surgery is shown with a double-hip spica cast, with a nerve catheter still inserted into the body exiting the spica cast at the top of the spica cast.

Orthopedic casts and their use are well understood in the art. An orthopedic cast may be formed by surrounding a portion of the body with cotton bandages infused with wet plaster of paris and allowing the plaster to harden, forming a hard shell. An exemplary orthopedic cast 12 may be a hip spica cast as depicted at 12. Alternatively, an orthopedic cast may be a body cast, or be a cast covering only a limb, a wrist, or any other portion or portions of the body. Differently, an orthopedic cast can be a different type of cast. The present invention encompasses any construction of a shell covering a portion of the body, irrespective of materials which may include fiberglass, thermoplastics, polyurethane, or other materials known in the art to be used to fabricate a cast.

Beneath the exemplary orthopedic cast 12 surrounding a portion of the body of the patient 2 is a catheter 4. The catheter has a forward end 6, which may also be known as the insertion end. The catheter 4 enters the body of the patient 2 through a body passage 14 of the patient 2. The portion of the catheter 4 situated inside the body passage 14 is also known in the art as the indwelling portion of the catheter 4. The catheter 4 has a distal end 8, which may also be known as the rearward end. Adjoining the distal end 8 of the catheter 4 may be an adapter 10, such as an industry-standard SnapLock adapter. Anesthesia being provided to the patient flows from its source, which may be an infusion pump or other source for delivering anesthesia, through a lumen joined to the adapter 10, then through the distal end 8 of the catheter 4, to the forward end 6 of the catheter 4, and into the body of the patient 2 through the indwelling portion of the catheter which is inserted into a body passage 14 of the patient 2. For a hip surgery, the body passage 14 of the patient 2 into which the indwelling portion of catheter 4 may be inserted is generally the front of the body at the crease between the leg and the hip. A catheter 4 may be a nerve catheter. Differently, a catheter 4 may be any tube, lumen, drain, or other device inserted in a body passage of the patient 14. The present invention encompasses the channeling of any catheter, tube, lumen, drain, or other device known in the art through a cast, from the site of its insertion or other coupling with a patient to the exterior of the cast.

FIGS. 2, 3, 4a and 4b are a perspective view, a side cross-sectional view, and two bottom cross-sectional views of an appliance for providing a channel through an orthopedic cast, in accordance with a preferred embodiment of the invention. FIG. 5 is a side cross-sectional view of an appliance for providing a channel through an orthopedic cast, in accordance with an alternate embodiment of the invention.

It will be appreciated by those with skill in the art that the terms "appliance for providing a channel through an orthopedic cast" or "container," as used in the instant application including in the preamble to the claims, do not limit the function of the apparatus to being an appliance, or to containing anything, nor do the terms limit the use of the apparatus to channels in orthopedic casts. Use of the term "appliance for providing a channel through an orthopedic cast" in any claim preambles is not intended to give life, meaning, or vitality to the claims. Further, applicant intends to use the terms "appliance" and "container" interchangeably.

In some embodiments, an appliance for providing a channel through an orthopedic cast 200 may have a generally oval shape, with a pair of flattened opposing sides 44, and a pair of curved opposing ends one of which is a catheter end 46 and one of which is a vacuum end 48. In some embodiments, an appliance for providing a channel through an orthopedic cast 200 may have a top surface 34 and a bottom surface 30.

In different embodiments, an appliance for providing a channel through an orthopedic cast 200 may have a shape other than a generally oval shape, such as a circular shape, a rectangular shape, a spherical shape, or any other geometric shape having any number of surfaces. The different embodiments will have at least an opening in a first surface, the opening leading to an interior section. In some embodiments, the interior section may therefore comprise a means for containing at least a portion of a medical device during construction of an orthopedic cast about the appliance. The different embodiments will also have at least a portion for removably coupling a vacuum source. In such embodiments the portion for removably coupling a vacuum source will include an opening in a second surface of the appliance 200 with which a vacuum source can be coupled. In some embodiments, the portion for removably coupling a vacuum source may therefore comprise a means for receiving a source of vacuum for suctionably adhering the appliance to a portion of a body about which an orthopedic cast is constructed. A divider is present in the embodiments for separating the first interior portion from the portion of the appliance to which the vacuum source is coupled, the portion being at least a second surface with an opening in the second surface with which a vacuum source is coupled.

In a preferred embodiment, an appliance for providing a channel through an orthopedic cast 200 may have a bottom opening 32 in the bottom surface 30. In such an embodiment, the bottom opening 32 leads to a first interior section 22. (FIGS. 11 and 12 may aid in comprehension of the remainder of this paragraph). In this embodiment, a portion of catheter 4 is rolled into a bundle, the bundle including an adapter 10 and the distal end 8 of the catheter 4, with the bundle being placed inside the first interior section 22. Then, appliance 200 is held against the patient 2, the appliance being held over the top of the body passage of the patient 14 where the indwelling portion of the catheter is situated. A vacuum source 300 is coupled to appliance 200 to keep appliance 200 in place while a cast is fabricated around a portion of the body of the patient 2.

In some embodiments, a divider separates the first interior section 22, the first interior section 22 containing the bundled distal portion 8 of the catheter 4 and adapter 10, from a portion of the appliance 200 for removably coupling a vacuum source. An opening in the divider permits the vacuum to create suction within the first interior section 22, the suction having a tendency to hold the appliance 200 against the patient 2.

Figure 3:
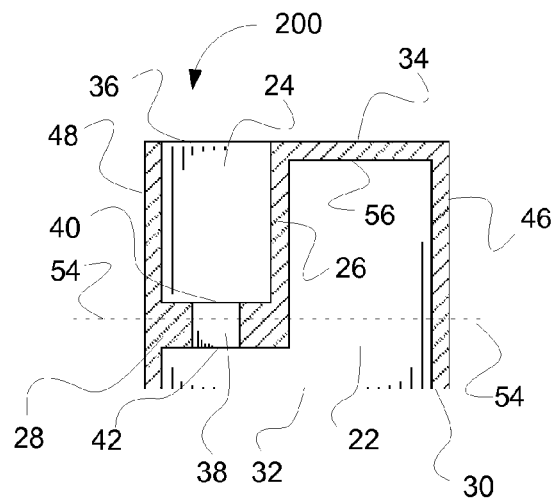
FIG. 3 is a side cross-sectional view of an appliance for providing a channel through an orthopedic cast, in accordance with an embodiment of the invention.

In some embodiments, such as that shown in FIG. 3, a portion of the appliance 200 for removably coupling a vacuum source is a second interior section 24 for removably coupling a vacuum source. In such embodiments, a top surface 34 of the appliance 200 has a top opening 36 leading to the second interior section 24. In some embodiments, the divider between the first interior section 22 and the second interior section 24 is at a base of the second interior section 24, the divider being opposite to the top surface 34 of the appliance 200. As shown clearly in FIG. 3, in some embodiments, the appliance 200 has a divider separating the first interior section 22 from the second interior section 24, the divider including a first interior wall 26 and a second interior wall 28, the two interior walls 26 and 28 being joined with one another at adjacent edges of the interior walls to form a corner.

Other configurations of divider are possible, for example, a divider being made up of only a single interior wall. Such design choices for a divider are within the grasp of those with skill in the art.

As shown in FIG. 5, in an alternate embodiment, an appliance 200 has a first interior section 22 for removably storing at least a portion of a catheter. In this alternate embodiment, there is no second interior section. In this embodiment, a portion of the appliance for removably coupling a vacuum source is a second surface of the appliance other than the bottom surface 30. In this embodiment, a second surface is a top surface 34. Top surface 34 includes a top opening 36 with which a vacuum source can be coupled. In this embodiment, a divider separating the first interior section 22 and the portion for removably coupling the vacuum source 36 is the top surface 34, the top surface 34 being the second surface including an opening with which a vacuum source can be coupled.

It will be apparent to those with skill in the art that the invention encompasses appliances including a container with at least a first interior section in which at least a portion of a catheter is stored, a portion of the appliance for removably coupling a vacuum source, a divider separating the first interior section from a portion of the appliance with which a vacuum source is coupled, and an opening in the divider separating the first interior section and the portion of the appliance for removably coupling a vacuum source. In some embodiments, such as that depicted in FIGS. 2, 3, 4a and 4b, the portion of the appliance with which a vacuum source is coupled is a second interior section. In different embodiments, such as that depicted in FIG. 5, the portion of the appliance with which a vacuum source is coupled is a surface of the appliance other than a bottom surface of the appliance. In different embodiments, an opening is any passage through which a vacuum can be induced, which may be one or more openings or any other type of passage. The design choice of such alternate embodiments including the configuration of the one or more interior sections, divider, surfaces and opening is within the grasp of those with skill in the art. All alternate embodiments meeting the above requirements are claimed within this appliance. However, the remainder of the application will focus on a preferred embodiment depicted in FIGS. 2, 3, 4a and 4b, among other figures.

Figure 4A:
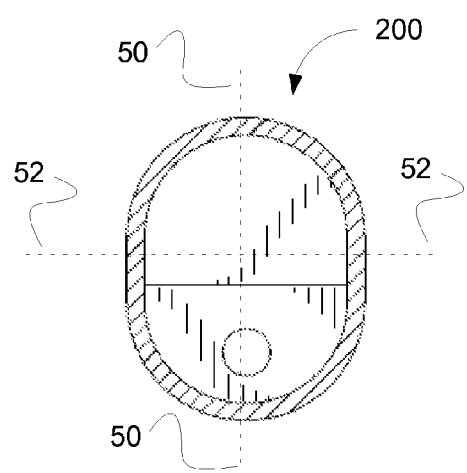
FIG. 4a is a bottom cross-sectional view of an appliance for providing a channel through an orthopedic cast, in accordance with an embodiment of the invention.
Figure 4B:
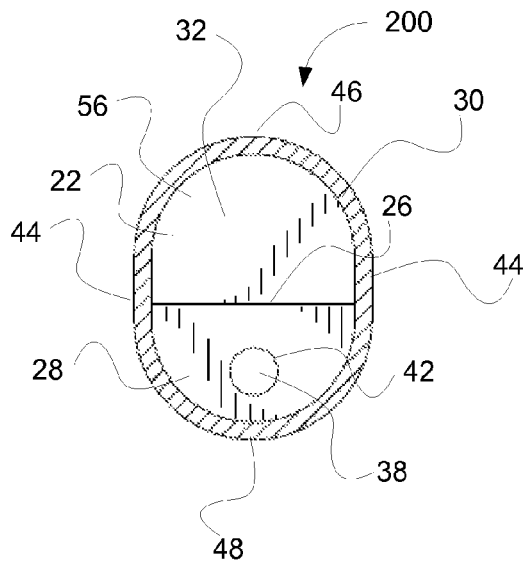
FIG. 4b is a bottom cross-sectional view of an appliance for providing a channel through an orthopedic cast, in accordance with an embodiment of the invention.
Figure 5:
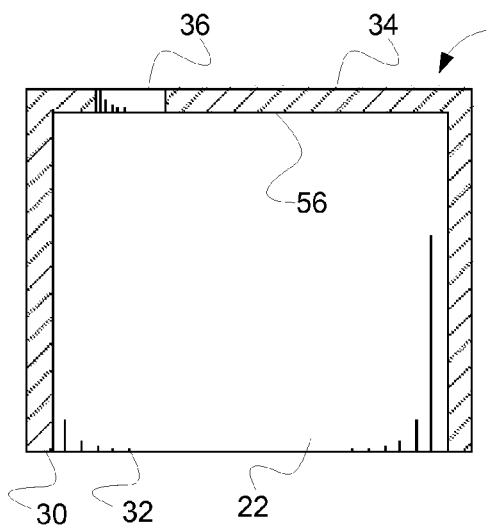
FIG. 5 is a side cross-sectional view of an appliance for providing a channel through an orthopedic cast, in accordance with an alternate embodiment of the invention.

In some embodiments, an appliance 200 includes a container having a generally oval shape in the horizontal cross-section, as seen in FIGS. 4a and 4b. The generally oval shape has a major axis 50 disposed between opposing ends of the generally oval shape. The generally oval shape has a minor axis 52 disposed between opposing sides of the generally oval shape. In a preferred embodiment, the length of the appliance 200 measured along the major axis 50 is approximately 9 centimeters, the width of the appliance 200 measured along the minor axis 52 is approximately 7 centimeters, and the height of the appliance 200 measured between the top surface 34 and the bottom surface 30 is approximately 8 centimeters. It will be appreciated by those with skill in the art that other dimensions of the appliance 200 are possible. In fact, for patients of varying size ranging from babies to full-grown adults, different dimensions of the appliance 200 are likely. Or, for catheters or other tubes inserted in a passage of the body in different parts of the body, different dimensions of the appliance 200 are likely. For example, it will be appreciated by those with skill in the art that an embodiment for use with an arm splint would likely be sized differently than an embodiment for use with a hip spica. In some embodiments, the length of the appliance 200 measured along the major axis 50 could range from 3 centimeters to 30 centimeters, while the width of the appliance 200 measured along the minor axis 52 could range from 2 centimeters to 30 centimeters, and the height of the appliance 200 measured between the top surface 34 and the bottom surface 30 could range from 2 centimeters to 30 centimeters.

In some embodiments, an appliance 200 has exterior walls of the flattened sides 44, catheter end 46 and vacuum end 48 having a thickness of approximately 5 millimeters. In some embodiments, an appliance 200 has a first interior wall 26 having a thickness of approximately 5 millimeters. In some embodiments, an appliance 200 has a second interior wall 28 having a thickness of approximately 10 millimeters. It will be appreciated by those with skill in the art that the thickness of the walls of the appliance 200 may be varied as needs for use of the appliance with various portions of the body or differently sized patients change. Accordingly, the thickness of the exterior and interior walls of the appliance may be as thin as 1 millimeter or as thick as 10 centimeters.

In some embodiments, the exterior and interior walls of the appliance 200 are made of plastic. In different embodiments, the exterior and interior walls of the appliance 200 are made of metal. In certain embodiments, the exterior and interior walls of the appliance 200 are made of material that render the appliance 200 suitable for autoclaving or otherwise sterilizing the appliance 200.

In some embodiments, the end of appliance 200 along the major axis 50 that is adjacent to the first interior section 22 is a catheter end 46, while the opposing end of the appliance that is adjacent to the second interior section 24 is a vacuum end 48. In the preferred embodiment, the opposing sides disposed at either end of the minor axis 52 are flattened sides 44, giving the horizontal cross-section the generally oval shape.

In some embodiments, a second interior wall 28 contains the plane of a horizontal cross-section 54 near the bottom surface 30 of the appliance 200. Viewing the side cross-section of FIG. 3, it can be seen that the divider separating the first interior section 22 from the second interior section 24 has a first interior wall 26 and a second interior wall 28 with a circular opening 38 in the second interior wall 28. This design permits the second interior section 24 to receive a hose from a vacuum source, while maximizing the size of the first interior section 22. Particularly, the base of the first interior section 22, the base being disposed adjacent to the bottom surface 30 of the appliance 200, covers the complete lateral area between the opposing ends and opposing sides of the appliance. This maximizes the coverage of the portion of the body 14 in which the indwelling portion of the catheter is contained by the appliance 200. The second interior wall 28 has a circular opening 38, which is the passage through which the vacuum source draws air out of the first interior section 22, the drawing of air having a tendency to adhere the appliance 200 to the patient 2 when the vacuum source is activated. The circular opening 38 has a top aperture 40 and a bottom aperture 42. In some embodiments, the circular opening 38 is a threaded circular opening 38. In such embodiments, the threaded circular opening 38 is configured to removably receive a threaded fitting which facilitates the coupling of a vacuum source.

Looking up into the appliance as seen in the bottom view of FIG. 4b, it can be seen that in the preferred embodiment, the appliance 200 has a bottom portion of the second interior wall 28 closest to the bottom surface 30 of the appliance 200, and a bottom portion 56 of the top surface 34 which constitutes the top of the first interior section 22. At the first interior wall 26, the first interior section 22 "steps up" in size from the portion of the first interior section 22 that is directly below the second interior section 24 to the portion of the first interior section 22 that is directly below the bottom portion 56 of the top surface 34. The first interior section 22 is "substantially" adjacent to the catheter end 46 of the appliance 200, where substantially means that the larger portion of the first interior section 22, the larger portion being the portion that extends from the bottom surface 30 to the top surface 34 of the appliance 200, is adjacent to the catheter end 46. A portion of the first interior section 22 is adjacent to the vacuum end 48 of the appliance 200, but that portion is a much smaller portion because it extends only from the bottom surface 30 to the second interior wall 28. It is the larger portion of the first interior section 22 that is adjacent to the catheter end 46; thus, the first interior section 22 is "substantially" adjacent to the catheter end 46 of the appliance 200.

In the preferred embodiment, the configuration of the first interior section 22, second interior section 24, and the circular opening 38 in the second interior wall 28 all serve to maximize the volume of space available for the bundled catheter 4 and adapter 10, while permitting connection of the vacuum source without having to turn the hose for the vacuum source inside the second interior section 24.

Figure 6:
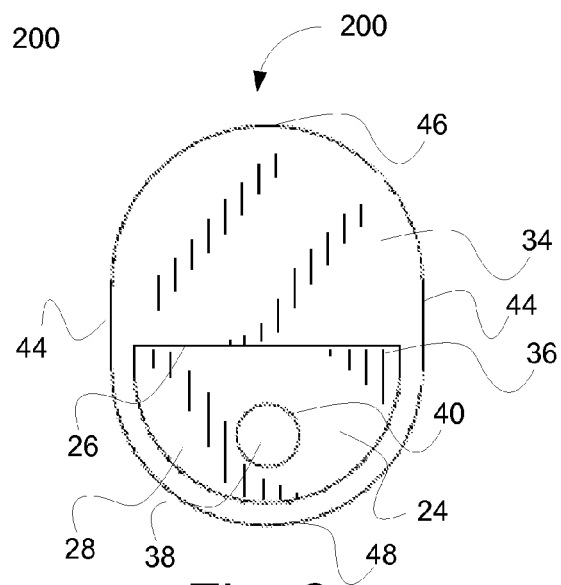
FIG. 6 is a top view of an appliance for providing a channel through an orthopedic cast, in accordance with an embodiment of the invention.
Figure 7:
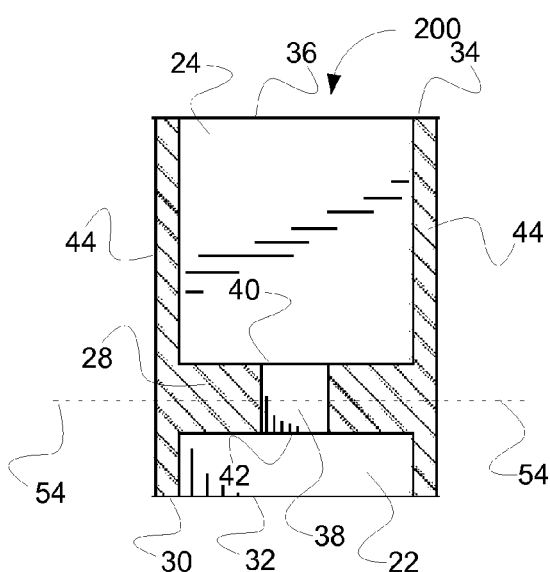
FIG. 7 is a front cross-sectional view of an appliance for providing a channel through an orthopedic cast, in accordance with an embodiment of the invention.

FIG. 6 is a top view of an appliance for providing a channel through an orthopedic cast, in accordance with an embodiment of the invention. FIG. 7 is a front cross-sectional view of an appliance for providing a channel through an orthopedic cast, in accordance with an embodiment of the invention.

In some embodiments, the "front" of the appliance 200 is defined by the vacuum end 48 of the appliance 200. This cross-sectional view of FIG. 7 shows a cross-section that slices through the appliance 200 at the center of the circular opening 38. In some embodiments, an appliance for providing a channel through an orthopedic cast 200 includes a top surface 34, the top surface 34 having a top opening 36 in the top surface 34. The top opening 36 leads to a second interior section 24, where the base of the second interior section 24 is formed by a second interior wall 28 that is parallel to the top surface 34. The second interior wall 28 is in a horizontal cross-section 54 that is near, but not in, the plane of the bottom surface 30 of the appliance 200. The second interior section 24 is also bounded by the inside wall of the vacuum end 48 of the appliance, and the portion of the first interior wall 26 and flattened sides 44 that are disposed nearest the vacuum end 48 of the appliance. The section interior wall 28 has a circular opening 38 through which air passes when the vacuum source is activated. The circular opening 38 has a top aperture 40 and a bottom aperture 42. Below the second interior section 24, adjacent to the opposing side of the second interior wall 28, is a portion of the first interior section 22, the portion of the first interior section 22 being located between the second interior wall 28 and the bottom opening 32 in the bottom surface 30 of the appliance 200.

Figure 8:
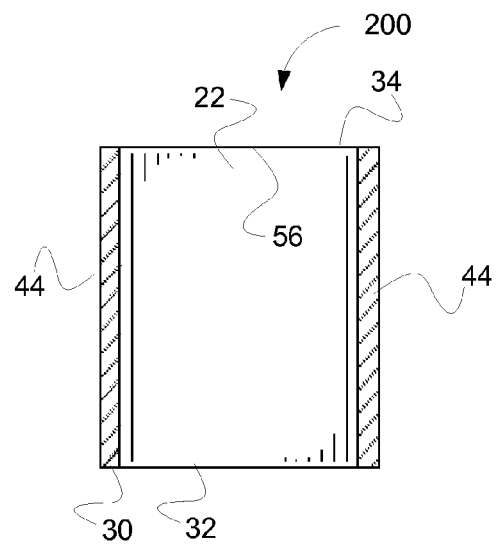
FIG. 8 is a front cross-sectional view of an appliance for providing a channel through an orthopedic cast, in accordance with an embodiment of the invention.
Figure 9:
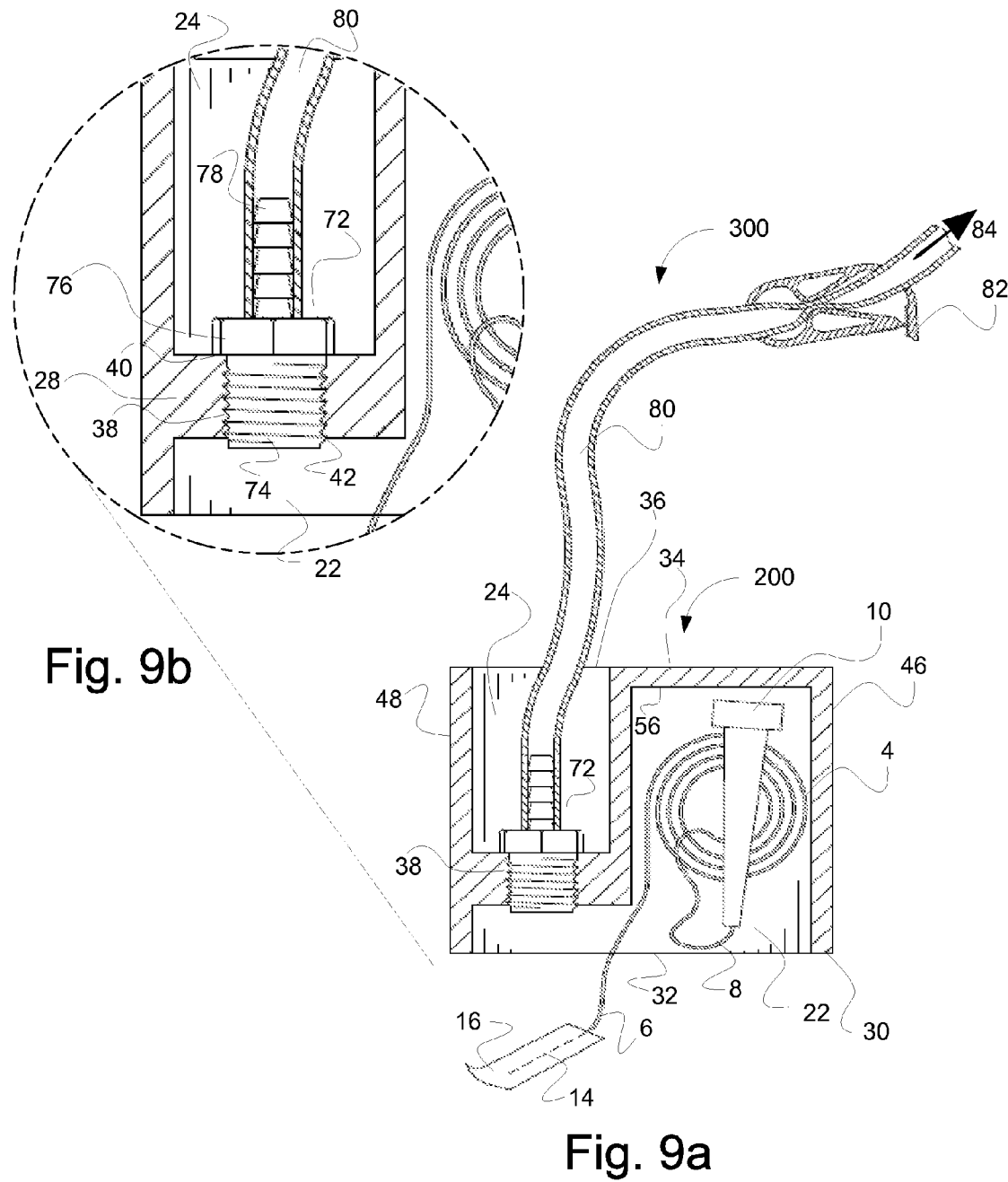
FIG. 9a is a side cross-sectional view of an appliance for providing a channel through an orthopedic cast, in accordance with an embodiment of the invention.
FIG. 9b is a detail view of a side cross-sectional view of an appliance for providing a channel through an orthopedic cast, in accordance with an embodiment of the invention.

FIG. 8 is a front cross-sectional view of an appliance for providing a channel through an orthopedic cast, in accordance with an embodiment of the invention. (Continued reference to FIG. 6 will aid in comprehension of the remainder of this paragraph). This cross-sectional view of FIG. 8 shows a cross-section that slices through the appliance 200 at a point inside the first interior section 22 that is between the catheter end 46 and the first interior wall 26 of the appliance 200, the cross-section being further from the "front" of the appliance defined by the vacuum end 48 than the cross-section of FIG. 7, but near the first interior wall 26 of the appliance 200. In some embodiments, an appliance for providing a channel through an orthopedic cast includes a top surface 34. Below the solid portion of the top surface 34, that is, the portion of the top surface 34 that does not include the top opening 36 of the top surface 34, is the first interior section 22. The first interior section is also bounded by the inside walls of the catheter end 46 and flattened sides 44 of the appliance, and the portion of the first interior wall 26 that is disposed nearest the catheter end 46 of the appliance. A portion of the first interior section 22 extends below a horizontal cross section 54 that is near, but not in, the plane of the bottom surface 30 of the appliance 200. This portion of the first interior section 22 also extends towards and is bounded by the interior wall of the vacuum end 48 of the appliance 200. Above this portion of the first interior section 22 is the second interior wall 28, the second interior wall 28 having a circular opening 38 through which air passes when the vacuum source is activated.

FIG. 9a is a side cross-sectional view of an appliance for providing a channel through an orthopedic cast, in accordance with an embodiment of the invention. FIG. 9b is a detail view of a side cross-sectional view of an appliance for providing a channel through an orthopedic cast, in accordance with an embodiment of the invention. In some embodiments, an appliance for providing a channel through an orthopedic cast 200 includes a first interior section 22, in which a bundle is placed, the bundle containing the distal portion 8 of a catheter 4 and a SnapLock adapter 10 attached to the catheter 4. The interior section 22 of the appliance 200 is accessed via a bottom opening 32 in the bottom surface 30 of the appliance. The portion of the catheter 4 that is not bundled or placed inside the appliance 200 remains in the tissue of the patient 2, inserted into a body passage 14 of the patient 2. This "indwelling" portion of the forward insertion end 6 of the catheter 4 is covered by a piece of tape 16 or other dressing adhered to the patient 2.

In some embodiments, a fitting 72 is inserted through the top opening 36 of the top surface 34 into the second interior section 24 of the appliance 200. The fitting is threaded into the circular opening 38 in the second interior wall 28 of the appliance 200, where the circular opening 38 is a threaded circular opening 38 with a diameter of 9⁄16". The fitting 72 may be a Diss-style 9⁄16" Male Hex Nut Vacuum/Suction Fitting with ¼" Hose Barb, or its equivalent. Such fittings are well known in the art. One source for such a fitting is Pneumatic Services, Inc., of Clearwater, Fla. The fitting 72 may have a hex nut section 76, which is disposed adjacent to the top aperture 40 of the circular opening 38. The 9⁄16" threaded portion 74 of the fitting 72 is threaded into the threaded circular opening 38 in the second interior wall 28 of the appliance 200. Opposing the threaded portion 74 of the fitting 72 is a ¼" hose barb 78, the hose barb 78 permitting the coupling of a hose 80 with an inside diameter of ¼".

In some embodiments, a vacuum source 300 is coupled with the appliance 200. In some embodiments, the vacuum source is the hospital suction 84 which is connected by hose 80 to the appliance 200 at the fitting 72. In some embodiments, a Dura Clamp 82 is threaded over the hose before the hose is connected to the hospital suction 84 or the fitting 72. A Dura Clamp is a "pinch clamp" which closes a hose threaded through the Dura Clamp by pinching the interior walls of the hose together. A Dura Clamp and its use are well known in the art. One source for a Dura Clamp is U.S. Plastic Corp., of Lima, Ohio. In some embodiments, when the appliance 200 is placed over the portion of the body including the body passage 14 of the patient 2 containing the indwelling portion of the catheter 4, hospital suction 84 is activated, creating a vacuum inside the hose 80 and the first interior section 22 of the appliance 200. The vacuum has a tendency to hold the appliance 200 in place against the patient 2, with the bundle contained within the first interior section 22 of the appliance 200. The Dura Clamp 82 can be closed, pinching off the hose 80. This permits the hospital suction 84 to be deactivated while maintaining the vacuum within the first interior section 22 of the appliance 200, and maintaining the position of the appliance 200 against the patient 2. A cast can then be fabricated around a portion of the patient 2. Other means of inducing a vacuum within the first interior section 22 of the appliance 200 are well known in the art, and all such means are encompassed within the 410 disclosure of this invention.

Figure 10:
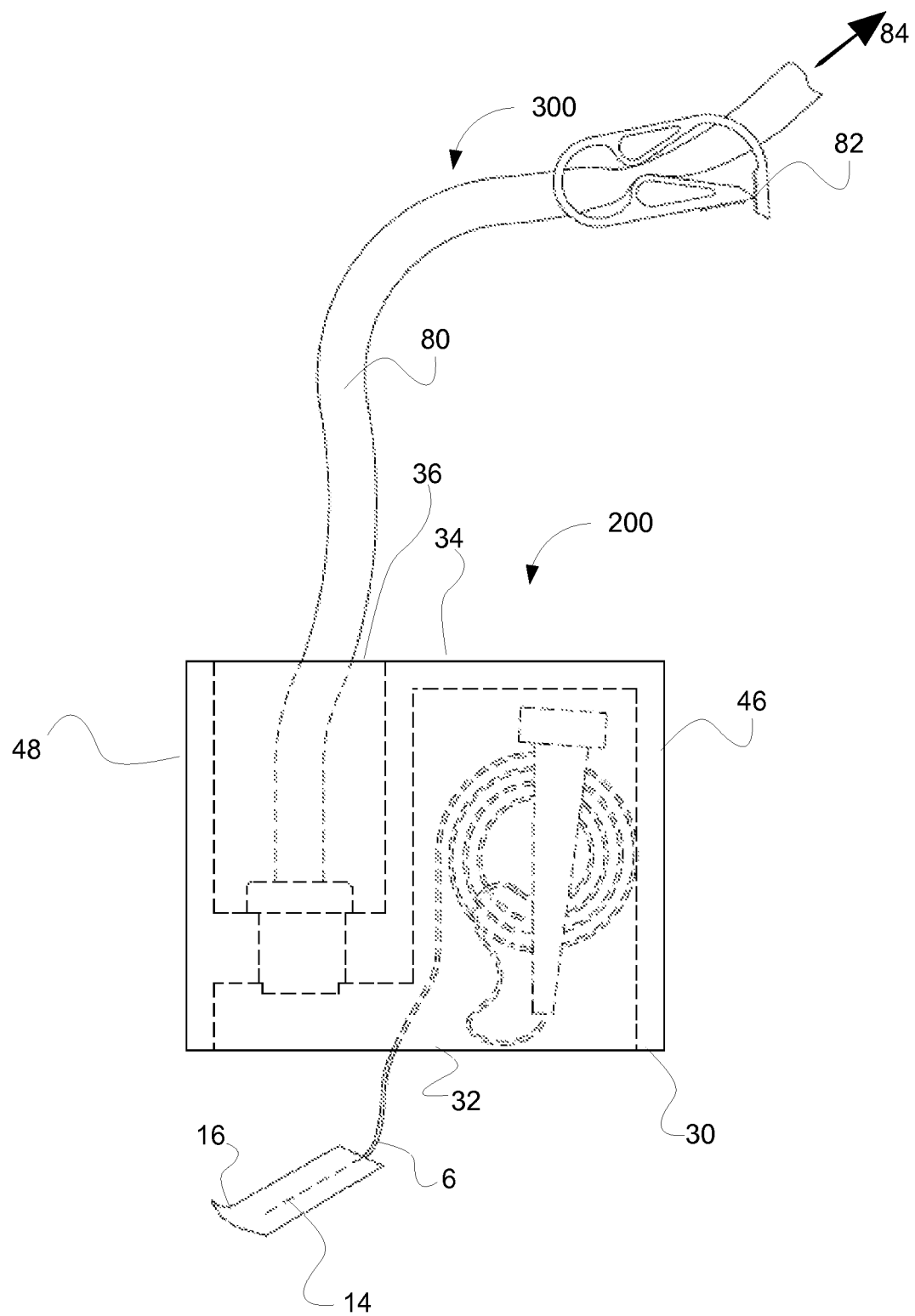
FIG. 10 is a side cutaway view of an appliance for providing a channel through an orthopedic cast, in accordance with an embodiment of the invention.

FIG. 10 is a side cutaway view of an appliance for providing a channel through an orthopedic cast, in accordance with an embodiment of the invention. In FIG. 10, a preferred embodiment is shown in which the bundle of the portion of the catheter 4 and the adapter 10 are shown in cutaway in the interior of the appliance 200. Below the appliance 200 are the forward insertion end 6 of the catheter 4, inserted into a body passage 14 of the patient 2, the indwelling portion of the catheter 4 being covered by a piece of tape 16 or other dressing.

Figure 11:
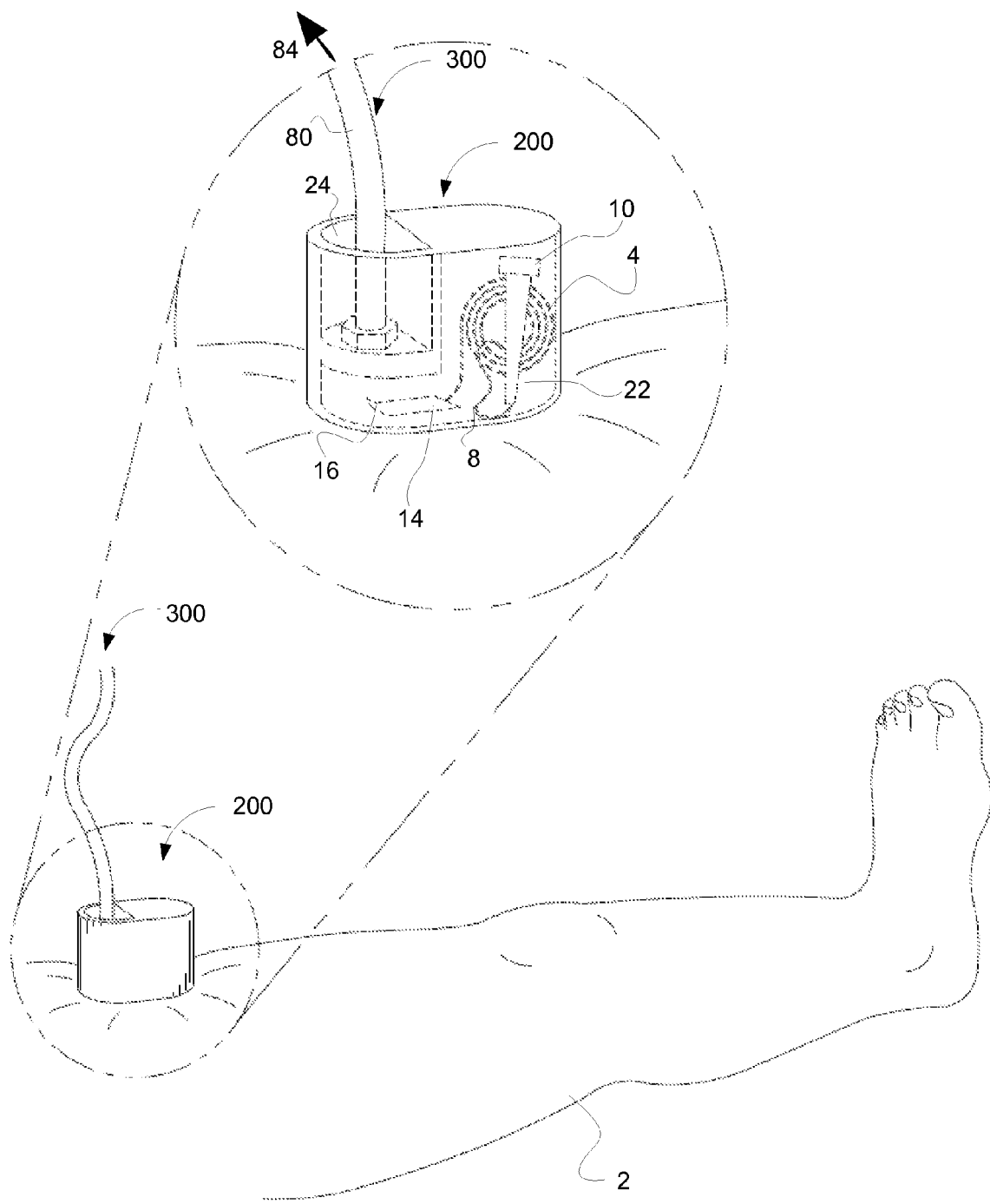
FIG. 11 is a perspective cutaway view of an appliance for providing a channel through an orthopedic cast, in accordance with an embodiment of the invention.

FIG. 11 is a perspective cutaway view of an appliance for providing a channel through an orthopedic cast, in accordance with an embodiment of the invention. In some embodiments, an appliance 200 is pressed against a portion of the body of the patient 2, the portion of the body including the body passage 14 of the patient 2 that contains the indwelling site of the catheter 4. The indwelling portion is covered with a piece of tape 16 or other dressing. The remainder of the catheter 4 and the SnapLock adapter 10 are bundled and tucked inside the first interior portion 22 of the appliance 200, prior to pressing the appliance 200 against the patient 2, with the bottom opening 32 of the appliance 200 covering the indwelling site of the catheter 4. The site where the catheter is inserted into a body passage 14 of the patient may be the crease where the leg and hip of the patient 2 are joined. Once the appliance 200 is held in position, a vacuum source 300 such as hospital suction 84 can be activated, drawing air out of the first interior section 22 and creating a vacuum in the first interior section 22, having a tendency to hold the appliance 200 in place against the body of the patient 2.

Figure 12:
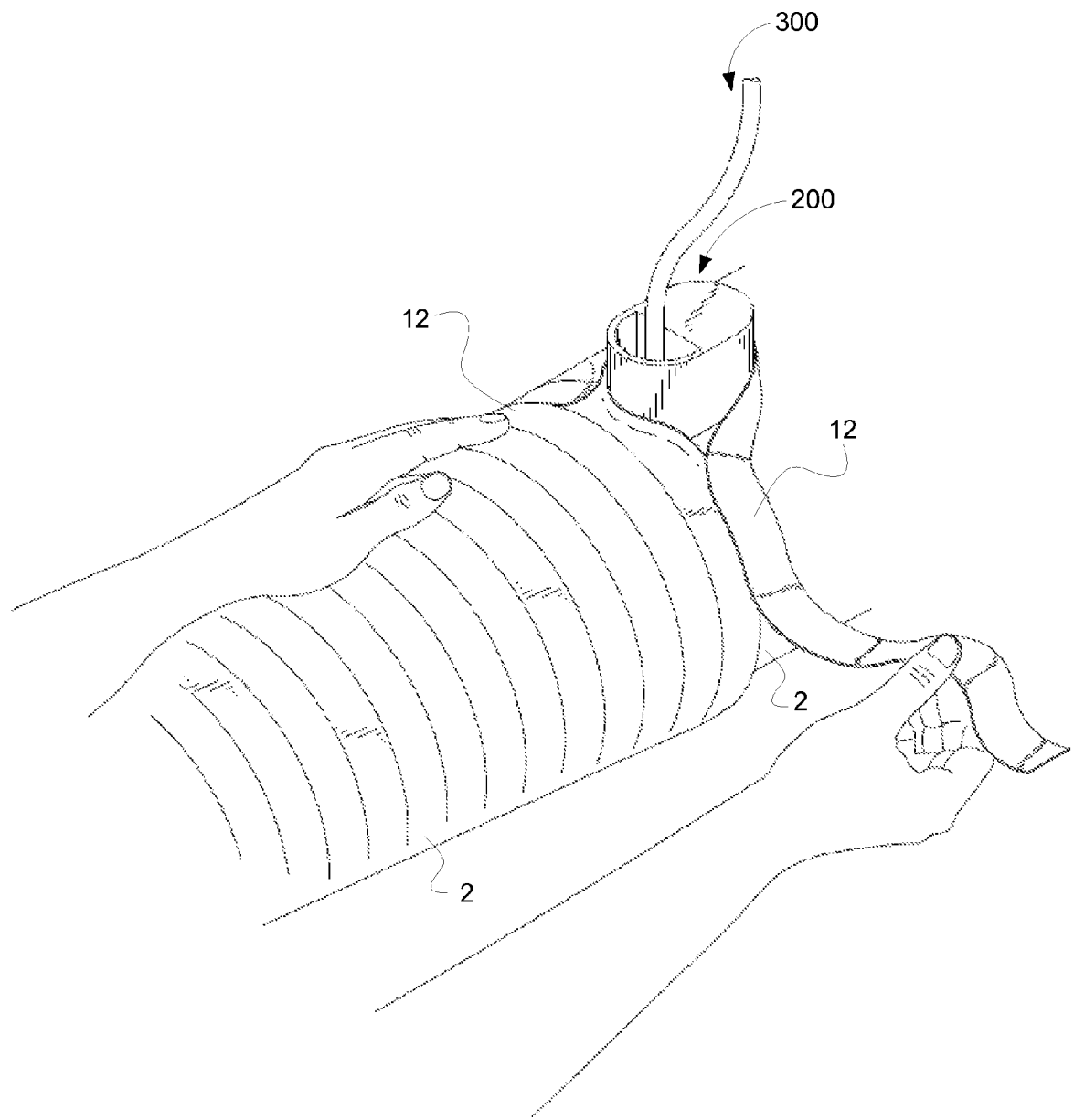
FIG. 12 is a perspective view of an appliance for providing a channel through an orthopedic cast, in accordance with an embodiment of the invention.

FIG. 12 is a perspective view of an appliance for providing a channel through an orthopedic cast, in accordance with an embodiment of the invention. Once the vacuum source 300 is activated, holding the appliance 200 in place against the body of the patient 2, the orthopedic cast 12 can be formed. In one embodiment, cotton bandages impregnated with plaster of paris that are dampened are applied around a limb or other portion of the body of the patient 2. The cast 12 is formed when the individual cotton bandages dry. Other materials and methods for forming a cast are well known in the art and are encompassed by the present invention. In some embodiments, portions of the exterior walls of the appliance 200 are spread with Surgilube lubricating jelly. Practitioners often cover their hands in Surgilube to ensure the bandages that form the cast 12 do not adhere to the hands of the practitioner. Likewise, in some embodiments, Surgilube spread over portions of the exterior walls of the appliance 200 will ensure that the bandages that form the cast 12 do not adhere to the appliance 200. Surgilube is well known in the art. One source for Surgilube is Allegro Medical, of Bolingbrook, Ill.

Figure 13:
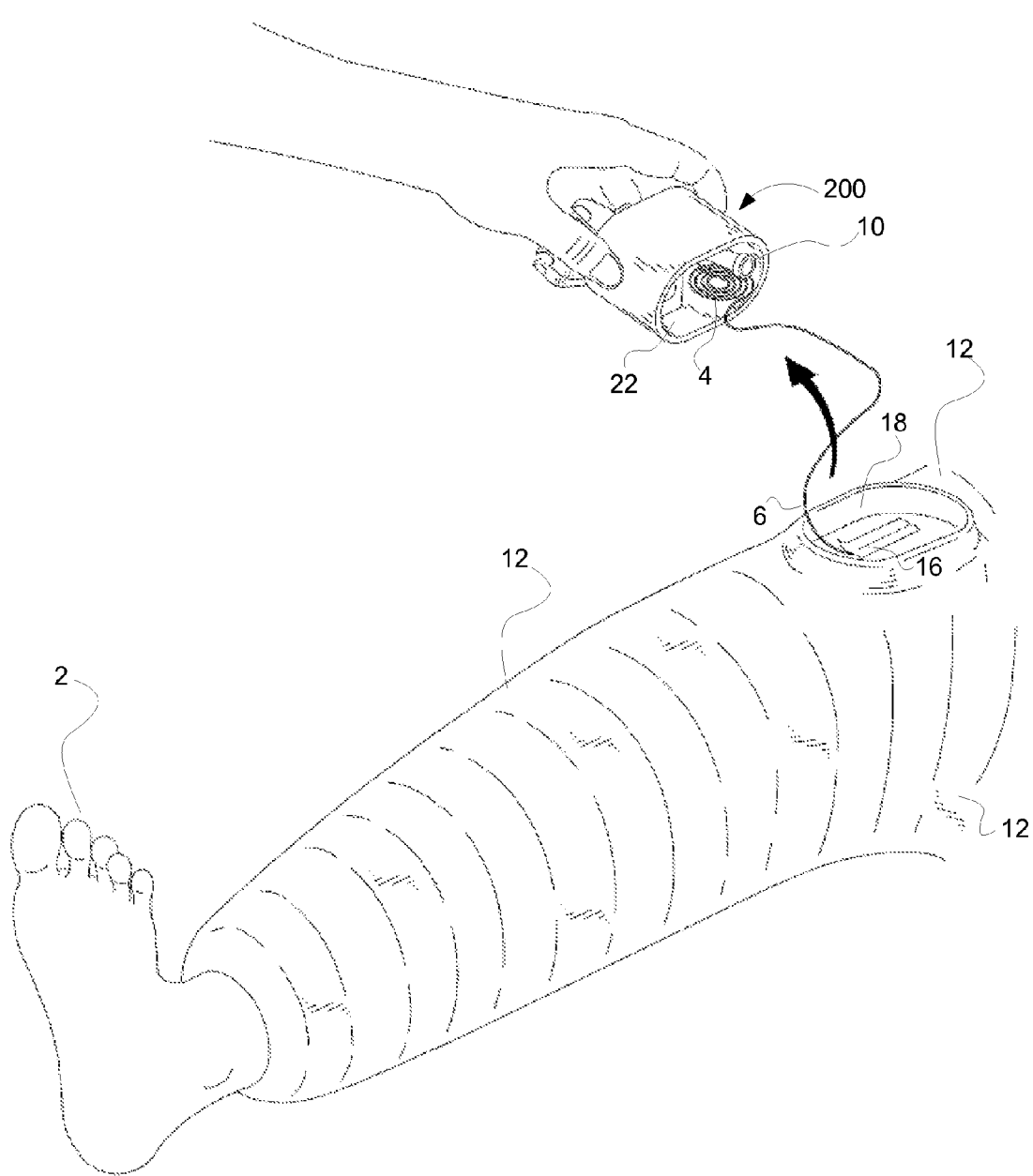
FIG. 13 is a perspective view of an appliance for providing a channel through an orthopedic cast, in accordance with an embodiment of the invention.

FIG. 13 is a perspective view of an appliance for providing a channel through an orthopedic cast, in accordance with an embodiment of the invention. In some embodiments, when a cast 12 has been fabricated and hardened, the vacuum source 300 is deactivated. In some embodiments, deactivating the vacuum source 300 may comprise releasing the Dura Clamp 82. Following the deactivation of the vacuum source 300, the appliance 200, with the bundle of the portion of the catheter 4 and the SnapLock adapter 10 contained in the first interior section 22 of the appliance 200, is removed from the cast 12, revealing a channel 18 in the formed cast, the channel 18 having a perimeter substantially corresponding to a perimeter defined by exterior wall(s) of the appliance 200. In some embodiments, the exterior wall(s) of the appliance 200 therefore may comprise a means for facilitating the formation of a channel in an orthopedic cast constructed about the appliance. Through the channel 18, the body passage 14 into which the catheter 4 is inserted can be viewed beneath the piece of tape 16 or other dressing.

Figure 14:
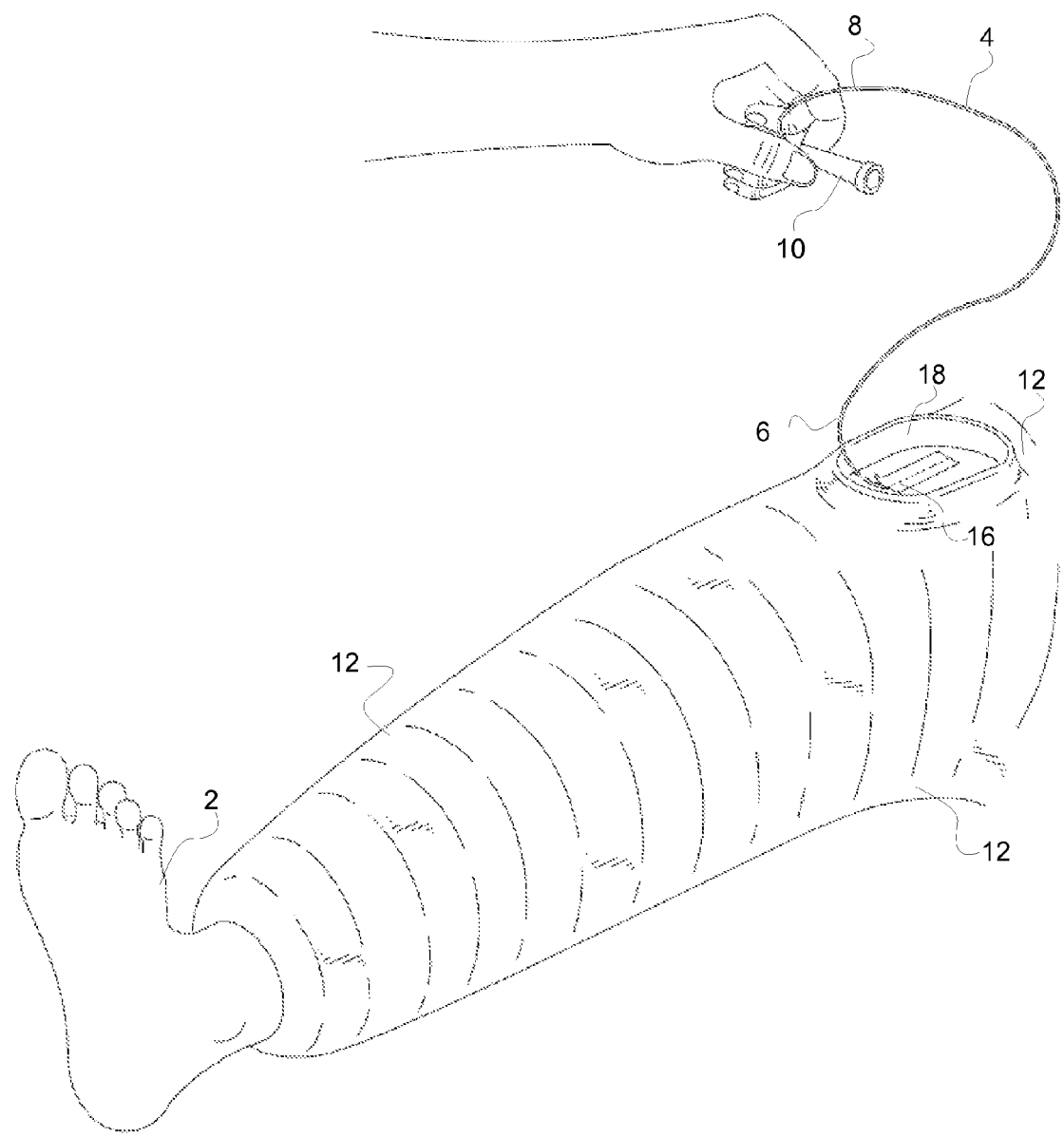
FIG. 14 is a perspective view of a channel through an orthopedic cast, in accordance with an embodiment of the invention.

FIG. 14 is a perspective view of a channel through an orthopedic cast, in accordance with an embodiment of the invention. In some embodiments, following removal of the appliance 200 from the cast 12 by pulling it away from the patient 2, the bundle of the portion of the catheter 4 and the SnapLock adapter 10 is removed from the first interior section 22 of the appliance 200. The appliance 200 can be autoclaved or otherwise sterilized and re-used. Utilizing the channel 18, anesthesia can then be delivered to the patient 2 by rejoining the connection between the infusion pump and the adapter 10 and activating the infusion pump.

FIG. 15 is a flow diagram of a method, in accordance with an embodiment of the invention. Method 400 may include one or more operations including operation 402, 404, 406, 408, 410, 412, 414, 416 and/or 418.

At operation 400, a method includes: bundling a portion of a catheter beginning at a distal end of the catheter, said bundling occurring without dislodging an insertion end of the catheter from a body passage through which the insertion end of the catheter is disposed, thereby rolling the portion of the catheter into a small bundle at 402; tucking the small bundle of the portion of the catheter into a first interior section of an appliance for providing a channel through an orthopedic cast at 404; holding a bottom surface of the appliance for providing a channel through an orthopedic cast against a first portion of the body, where the first portion of the body includes the body passage through which the insertion end of the catheter is disposed, and where an aperture in the bottom surface of the appliance for providing a channel through an orthopedic cast is disposed adjacent to the first portion of the body, said aperture leading to the first interior section of the appliance for providing a channel through an orthopedic cast, said first interior section containing the small bundle of the portion of the catheter at 406; removably coupling a vacuum source with the appliance for providing a channel through an orthopedic cast at 408; releasing the hold on the appliance for providing a channel through an orthopedic cast, thereby allowing the vacuum source to maintain the position of the appliance for providing a channel through an orthopedic cast against the first portion of the body at 410; applying strips of material around a second portion of the body and around the appliance for providing a channel through an orthopedic cast, thereby forming a cast around the second portion of the body with the appliance for providing a channel through an orthopedic cast protruding through a channel in the formed cast at 412; removing the vacuum source from the appliance for providing a channel through an orthopedic cast at 414; removing the appliance for providing a channel through an orthopedic cast from the channel formed in the cast at 416; and unrolling the catheter from its small bundle at 418.

While preferred and alternative embodiments of the invention have been illustrated and described, as noted above, many changes can be made without departing from the spirit and scope of the invention. Accordingly, the scope of the invention is not limited by the disclosure of these preferred and alternate embodiments. Instead, the invention should be determined entirely by reference to the claims that follow.

What is claimed is:

1. An appliance for providing a channel through an orthopedic cast, comprising:
   a container, including at least:
      a first interior section for removably storing at least a portion of a medical device;
      a portion for removably coupling a vacuum source;
      a divider separating the first interior section and the portion for removably coupling a vacuum source;
      a bottom surface including at least a bottom opening through which at least a portion of a medical device to be stored can be inserted into the first interior section;
      a second surface including at least a vacuum opening with which a vacuum source can be coupled to the portion for removably coupling a vacuum source; and
      a passage through the divider separating the first interior section and the portion for removably coupling a vacuum source.

2. The appliance of claim 1, wherein the portion for removably coupling a vacuum source is a second interior section for removably coupling a vacuum source, and wherein the second surface including at least a vacuum opening with which a vacuum source can be coupled to the portion for removably coupling a vacuum source is a top surface of the container including at least a top opening through which a vacuum source can be inserted into the second interior section for removably coupling a vacuum source.

3. The appliance of claim 2, wherein the divider separating the first interior section and the second interior section includes at least a first interior wall separating the first interior section and the second interior section and a second interior wall separating the first interior section and the second interior section.

4. The appliance of claim 3, wherein the container has a generally oval shape in the horizontal cross section, the generally oval shape in the horizontal cross section having a major axis disposed between the opposing ends of the container, the generally oval shape in the horizontal cross section having a minor axis disposed between the opposing sides of the container.

5. The appliance of claim 4, wherein the opposing sides of the container are flattened so as to be parallel with the major axis disposed between the opposing ends of the container.

6. The appliance of claim 5, wherein the first interior section is disposed substantially adjacent to a first end of the container, the first end of the container being a catheter end of the container, and wherein the second interior section is disposed adjacent to a second end of the container opposing the first end of the container, the second end of the container being a vacuum end of the container.

7. The appliance of claim 6, wherein the first interior wall separating the first interior section and the second interior section is parallel to the minor axis disposed between the opposing sides of the container, and wherein the first interior wall separating the first interior section and the second interior section is disposed between the top surface of the container and a horizontal cross section of the container near the bottom surface of the container.

8. The appliance of claim 7, wherein the second interior wall separating the first interior section and the second interior section is in the plane of the horizontal cross section of the container near the bottom surface of the container, and wherein the second interior wall separating the first interior section and the second interior section is disposed between the vacuum end of the container and the first interior wall separating the first interior section and the second interior section.

9. The appliance of claim 8, wherein the second interior wall includes at least an opening in the second interior wall, wherein the opening in the second interior wall is a circular opening.

10. The appliance of claim 9, wherein the opening in the second interior wall is a threaded circular opening.

11. The appliance of claim 1, wherein the container is fabricated of material that renders the container suitable for being autoclaved or otherwise sterilized.

12. The appliance of claim 1, wherein the portion for removably coupling a vacuum source comprises:
 at least one of a hose barb or a nozzle, the at least one of a hose barb or nozzle configured for removably receiving a hose coupled to a vacuum source.

13. The appliance of claim 1, wherein the first interior section for removably storing at least a portion of a medical device comprises:
 a first interior section for removably storing at least a portion of at least one of one or more catheters, one or more lumen, one or more tubes, one or more drains, one or more lines, one or more needles, or one or more wires.

14. A method for fabricating an orthopedic cast, comprising:
 bundling a portion of a catheter beginning at a distal end of the catheter, said bundling occurring without dislodging an insertion end of the catheter from a body passage through which the insertion end of the catheter is disposed, thereby rolling the portion of the catheter into a small bundle;
 tucking the small bundle of the portion of the catheter into a first interior section of an appliance for providing a channel through an orthopedic cast;
 holding a bottom surface of the appliance for providing a channel through an orthopedic cast against a first portion of the body, where the first portion of the body includes the body passage through which the insertion end of the catheter is disposed, and where an aperture in the bottom surface of the appliance for providing a channel through an orthopedic cast is disposed adjacent to the first portion of the body, said aperture leading to the first interior section of the appliance for providing a channel through an orthopedic cast, said first interior section containing the small bundle of the portion of the catheter;
 removably coupling a vacuum source with the appliance for providing a channel through an orthopedic cast;
 releasing the hold on the appliance for providing a channel through an orthopedic cast, thereby allowing the vacuum source to maintain the position of the appliance for providing a channel through an orthopedic cast against the first portion of the body;
 applying strips of material around a second portion of the body and around the appliance for providing a channel through an orthopedic cast, thereby forming a cast around the second portion of the body with the appliance for providing a channel through an orthopedic cast protruding through a channel in the formed cast;
 removing the vacuum source from the appliance for providing a channel through an orthopedic cast;
 removing the appliance for providing a channel through an orthopedic cast from the channel formed in the cast; and
 unrolling the catheter from its small bundle.

15. A system, comprising:
 a vacuum source;
 one or more catheter components, including at least a catheter adapter coupled with a lumen; and
 an appliance configured for providing a channel through an orthopedic cast, including at least:
  an interior section of the appliance, the interior section configured for storing at least the catheter adapter, the interior section of the appliance accessible via an opening in a surface of the appliance; and
  a port configured for coupling the vacuum source with the appliance.

16. The system of claim 15, further comprising:
 a portion of lubricating jelly,
 wherein the appliance configured for providing a channel through an orthopedic cast includes at least:
  at least one exterior surface configured for receiving at least some of the lubricating jelly, the lubricating jelly operable to facilitate separation of the appliance from a cast formed about the appliance.

* * * * *